US010294198B2

(12) United States Patent
Halpaap et al.

(10) Patent No.: US 10,294,198 B2
(45) Date of Patent: May 21, 2019

(54) METHOD FOR PRODUCING XYLYLENE DIISOCYANATES IN THE GASEOUS PHASE (71) Applicant: Covestro Deutschland AG, Leverkusen (DE)

(72) Inventors: Reinhard Halpaap, Odenthal (DE); Ralph Weber, Leichlingen (DE); Josef Sanders, Leverkusen (DE); Frank Richter, Leverkusen (DE); Elsa Karoline Schadlich, Bonn (DE); Armin Schymura, Neuss (DE); Martin Ehrig, Leverkusen (DE); Sebastian Hoch, Freiburg im Breisgau (DE); Robert Maleika, Dusseldorf (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 185 days.

(21) Appl. No.: 15/302,724

(22) PCT Filed: Apr. 13, 2015

(86) PCT No.: PCT/EP2015/057956
§ 371 (c)(1),
(2) Date: Oct. 7, 2016

(87) PCT Pub. No.: WO2015/155365
PCT Pub. Date: Oct. 15, 2015

(65) Prior Publication Data
US 2017/0210702 A1 Jul. 27, 2017

(30) Foreign Application Priority Data
Apr. 11, 2014 (EP) .................................... 14164345

(51) Int. Cl.
C07C 263/10 (2006.01)
G02B 1/04 (2006.01)
C08G 18/24 (2006.01)
C08G 18/38 (2006.01)
C08G 18/71 (2006.01)
C08G 18/75 (2006.01)
C08G 18/76 (2006.01)
C08K 5/521 (2006.01)
C08L 75/04 (2006.01)
C08L 81/00 (2006.01)
C07C 265/14 (2006.01)

(52) U.S. Cl.
CPC .......... C07C 263/10 (2013.01); C08G 18/242 (2013.01); C08G 18/3865 (2013.01); C08G 18/3868 (2013.01); C08G 18/3876 (2013.01); C08G 18/714 (2013.01); C08G 18/758 (2013.01); C08G 18/7642 (2013.01); C08K 5/521 (2013.01); C08L 75/04 (2013.01); G02B 1/041 (2013.01); C08G 2125/00 (2013.01)

(58) Field of Classification Search
CPC .............. C07C 263/10; C08G 18/3876; C08G 18/7642; C08G 18/3865; C08G 18/714; C08G 18/242; C08G 18/758; C08G 18/3868; C08G 2125/00; C08K 5/521; C08L 75/04; G02B 1/041
See application file for complete search history.

(56) References Cited

U.S. PATENT DOCUMENTS

| 3,424,780 | A | 1/1969 | Sayigh |
| 4,774,264 | A | 9/1988 | Weber et al. |
| 4,847,408 | A | 7/1989 | Frosch et al. |
| 5,126,170 | A | 6/1992 | Zwiener et al. |
| 5,306,799 | A | 4/1994 | Kobayashi et al. |
| 5,391,683 | A | 2/1995 | Joulak et al. |
| 5,502,147 | A | 3/1996 | Nodelman et al. |
| 5,523,467 | A | 6/1996 | Okazaki et al. |
| 5,679,839 | A | 10/1997 | Armand et al. |
| 6,225,497 | B1 | 5/2001 | Becker et al. |
| 6,316,662 | B1 | 11/2001 | Woo et al. |
| 6,506,811 | B2 | 1/2003 | Woo et al. |
| 6,706,913 | B2 | 3/2004 | Leimkuhler et al. |
| 6,730,768 | B2 | 5/2004 | Heidbreder et al. |
| 6,800,781 | B2 | 10/2004 | Herold et al. |
| 6,838,578 | B2 | 1/2005 | Leimkuhler et al. |
| 6,930,199 | B2 | 8/2005 | Meyn et al. |
| 7,019,164 | B2 | 3/2006 | Friedrich et al. |
| 7,754,915 | B2 | 7/2010 | Herold et al. |
| 8,692,016 | B2 | 4/2014 | Sanders et al. |
| 2010/0234552 | A1 | 9/2010 | Kitahara |
| 2012/0095255 | A1 | 4/2012 | Mattke et al. |

FOREIGN PATENT DOCUMENTS

| DE | 2948419 A1 | 8/1981 |
| DE | 19701835 A1 | 7/1998 |
| EP | 0689556 A1 | 1/1996 |
| EP | 0978523 A1 | 2/2000 |
| EP | 1640394 A1 | 3/2006 |

(Continued)

OTHER PUBLICATIONS

N. Adam et al: "Polyurethanes" Ullmann's Encyclopedia of Industrial Chemistry, Electronic Release, 7th ed., Chap. 3.2-3.4, Wiley VCH, Weinheim 2005.

(Continued)

Primary Examiner — Rabon A Sergent
(74) Attorney, Agent, or Firm — John E. Mrozinski, Jr.

(57) ABSTRACT

The invention relates to a method for producing the isomers 1,3- and/or 1,4-xylylene diisocyanates by reacting the corresponding 1,3- and/or 1,4-xylylene diamines with phosgene in the gaseous phase.

12 Claims, 1 Drawing Sheet

(56) References Cited

FOREIGN PATENT DOCUMENTS

| EP | 1908749 A1 | 4/2008 |
| GB | 1534258 | 11/1978 |
| JP | 07118263 A | 5/1999 |
| WO | 2013079517 A1 | 6/2013 |

OTHER PUBLICATIONS

Kunststoff-Handbuch, vol. VII, edited by Vieweg and Hochtlen, Carl-Hanser-Verlag, Munich 1966, pp. 108 and 109, 453 to 455, and 507 to 510.

METHOD FOR PRODUCING XYLYLENE DIISOCYANATES IN THE GASEOUS PHASE

CROSS-REFERENCE TO RELATED APPLICATION

This application is a national stage application (under 35 U.S.C. § 371) of PCT/EP2015/057956, filed Apr. 13, 2015, which claims benefit of European Application No. 14164345.2, filed Apr. 11, 2014, both of which are incorporated herein by reference in their entirety.

FIELD OF THE INVENTION

The invention relates to a method for producing the isomeric 1,3- and/or 1,4-xylylene diisocyanates (1,3-XDI and/or 1,4-XDI, also referred to, individually or in a mixture, as XDI) by reaction of the corresponding 1,3- and/or 1,4-xylylenediamines (1,3-XDA and/or 1,4-XDA, also referred to, individually or in a mixture, as XDA) with phosgene in the gas phase.

1,3-xylylenediamine (1,3-XDA)
1,3-bis(aminomethyl)benzene 1,3-xylylene diisocyanate (1,3-XDI)
1,3-bis(isocyanatomethyl)benzene

BACKGROUND OF THE INVENTION

Isocyanates are produced in large volumes and serve primarily as starting materials for producing polyurethanes. They are mostly produced by reaction of the corresponding amines with phosgene. A distinction is made here between aromatic isocyanates, where the NCO groups are bonded directly to an aromatic ring, and aliphatic or cycloaliphatic isocyanates, where the NCO groups are bonded to an aliphatic, sp3-hybridized C atom.

XDI is an aliphatic diisocyanate with benzylically bonded NCO groups of very specific reactivity.

On account of the high reactivity thereof by comparison with aliphatic polyisocyanates, and the more favorable toxicological properties by comparison with polyisocyanates having aromatically bonded NCO groups, XDI and/or XDI polyisocyanates is/are used advantageously for the adhesive bonding of food packaging. On account of its high refractive index in combination with high light stability, the 1,3-isomer in particular is used for producing optical lenses and spectacle lenses.

The production of XDI in the liquid phase is known practice. EP 0 384 463 B1 claims a process for producing XDI that is characterized by the preparation of XDA hydrochloride in a first reaction stage, at or below 30° C., in an ester as solvent, with the amine hydrochloride being phosgenated in a second reaction step at 120-170° C. The objective of this specific reaction regime is to keep the level of the chloromethyl benzylisocyanate by-product formed at a low level. U.S. Pat. No. 5,523,467 claims a process for producing aliphatic polyisocyanates that is characterized first by reaction of aliphatic polyamines, their hydrochlorides or carbonates with phosgene in an inert solvent, the reaction then being continued with additional introduction of an inert gas. Under the conditions of the inert gas introduction, the phosgene excess in the production of the XDI can be kept at a lower level, and the formation of unwanted tar during the reaction can be reduced. A disadvantage of this method is that it is a multistage batch operation which is carried out in high dilution in a relatively high-boiling solvent and requires long reaction times. The laborious XDI production method is complex, energy-intensive, and therefore expensive.

EP 1 908 749 A1 describes the phosgenation of amine hydrochlorides, particularly of 1,3-XDA hydrochloride, where the amine hydrochlorides are produced under superatmospheric pressure, in order to control the particle size in the suspension, in order to lower the viscosity of the slurry, and in order to generate a low level of secondary components, especially of 3-chloromethyl benzylisocyanate, during the phosgenation. The heterogeneous phosgenating reaction of the salts of XDA in high dilution in specific solvents while observing a defined reaction regime in order to avoid the formation of tar or of the unwanted secondary component 3- and/or 4-chloromethyl benzylisocyanate (3-chloroxylylene isocyanate or 3-Cl-XI; 4-chloroxylylene isocyanate or 4-Cl-XI, also referred to, individually or in a mixture, as Cl-XI) is difficult to realize and is accompanied by large losses in yield.

All of these difficulties have to date stood in the way of the more broad use of XDI.

One particularly economic possibility for the production of isocyanates is the reaction of the corresponding amines with phosgene in the gas phase.

EP 0 289 840 B1 describes a method for producing (cyclo)aliphatic diisocyanates by phosgenation of the corresponding, vaporous (cyclo)aliphatic diamines at 200° C. to 600° C. Phosgene is supplied in a stoichiometric excess. The superheated streams of vaporous (cyclo)aliphatic diamine or (cyclo)aliphatic diamine/inert gas mixture, on the one hand, and of phosgene, on the other, are passed continuously into a cylindrical reaction space, where they are mixed with one another and reacted. During the exothermic phosgenating reaction, a turbulent flow is maintained.

EP-A 0 928 785, EP-A 1 319 655, EP-A 1 555 258, EP-A 1 275 639, EP-A 1 275 640, EP-A 1 403 248 and EP-A 1 526 129 describe specific embodiments for this technology, which, however, relate to the reactor per se and the reaction regime, without addressing in more detail the vaporizer technology used in the pretreatment of the reactants.

EP 0 593 334 B1 (U.S. Pat. No. 5,391,683) and EP 0 699 657 B1 (U.S. Pat. No. 5,679,839) claim methods for producing aromatic polyisocyanates. The reaction of xylylenediamine, as well as tolylenediamine and phenylenediamine, with phosgene is mentioned, but the reference in both cases is to diaminoxylene. US 2012/0095255 A claims a method for producing isocyanates wherein an amine and phosgene can be mixed with one another and reacted in the gas phase. One dependent claim (claim 26) also claims the reaction of p-xylylenediamine, within a long series of mono-, di-, and triamines. None of these applications contains any references to the particular difficulties which arise with the vaporization of XDA, or the overcoming of these difficulties.

EP 1 754 698 B1 describes a method for producing isocyanates by phosgenation of amines in the gas phase, wherein the amines are heated in liquid form, vaporized and/or superheated in gas form using one or more heat exchangers having a volume-specific heat exchanger area for the amine side of at least 1000 m$^2$/m$^3$ and which, for guiding the flow of the amines, have channels which possess a hydraulic diameter of 1000 to 10 000 µm. This method as well is not suitable for phosgenating XDA, since the small dimensions of the channels of these heat exchangers mean that they very quickly become blocked by the xylylenepolyamines which form, these polyamines being of high viscosity and becoming solid on further temperature exposure.

WO 2013 079517 A1 describes a specific method for producing isocyanates by gas-phase phosgenation. In this particular embodiment, a method for producing isocyanates by phosgenation of the corresponding amines in a fluidized-bed reactor is claimed, the method being characterized in that a gas stream containing the phosgene is utilized as fluidizing gas to maintain an inert solid in suspension, and in that a liquid stream containing the amine is metered into the fluidized bed, with the amine undergoing partial or complete vaporization and reacting with the phosgene to give a reaction gas mixture comprising the corresponding isocyanate, which is taken off from the fluidized-bed reactor. The utilization of the heat of reaction for vaporization and superheating of the amines in the fluidized bed is seen as an advantage. What that specification conveys is that the only amines suitable for gas-phase phosgenation are thermally stable amines which undergo only a relatively low degree of decomposition at the high vaporization temperatures required—at most 2 mol %, more preferably at most 1 mol %, or very preferably at most 0.5 mol %. These thermally stable amines include aliphatic diamines and aromatic diamines, which are listed by way of example in the specification. Benzylic amines do not belong to this group, as described below on the basis of our own results.

As our own experiments, however, have shown, the gas-phase methods according to the prior art described cannot be used readily for the phosgenation of XDA, since XDAs form nonvolatile xylylene-polyamines even at temperatures well below their boiling temperature, giving off ammonia as they do so. As a result, after just a short time, there is an increase in viscosity, there is fouling and clogging in the amine vaporizer, and there is fouling caused by deposition of ammonium chloride in the reactor and in the downstream offgas system.

In summary it may be stated that to date no method from the prior art is suitable for the production of XDI in the gas phase. Consequently there continued to be a great need for a simple and inexpensive method for producing XDI in the gas phase, avoiding the disadvantages described for the methods of the prior art.

SUMMARY OF THE INVENTION

Surprisingly it has now been found that in spite of the difficulties described, XDI can be produced in good yields with sufficiently long plant run times by vaporizing the corresponding XDA at a pressure of <1000 mbar abs., with the mean residence time in the vaporizer circuit being 5 to 90 minutes, the temperature in the pumping circuit of the vaporization being 40 to 190° C., and the XDA vapors, heated a further 10-100° K above the vaporization temperature of the XDA under the prevailing pressure, being subsequently reacted with phosgene by known methods of gas-phase phosgenation.

A particular surprise is that under these drastic reaction conditions, the highly sensitive XDA does not—as would actually be expected in accordance with the heating trials conducted—tend to form by-products such as ammonia and nonvolatile xylylenepolyamines, for example, and that even in the crude product the CI-XI content is typically in the range between 0.1 to 0.5 wt % based on the sum of XDI and CI-XI.

These and other advantages and benefits of the present invention will be apparent from the Detailed Description of the Invention herein below.

BRIEF DESCRIPTION OF THE FIGURES

The present invention will now be described for purposes of illustration and not limitation in conjunction with the FIGURES, wherein.

DETAILED DESCRIPTION OF THE INVENTION

The present invention provides a method for producing 1,3- and/or 1,4-xylylene diisocyanate (XDI) by phosgenation of 1,3- and/or 1,4-xylylenediamine (XDA) with phosgene in the gas phase, characterized in that the xylylenediamine/xylylenediamines, optionally with addition of stabilizers and/or an inert gas, a) is/are vaporized at <1000 mbar abs., preferably at 350 to 900 mbar abs., more preferably at 500 to 800 mbar abs., with b) the mean residence time in the vaporizer circuit being 5 to 90 minutes, preferably 10 to 60 minutes, more preferably 10 to 45 minutes, c) the temperature in the pumping circuit of the vaporization being 40 to 190° C., preferably 60 to 170° C., more preferably 60 to 150° C., and d) the XDA vapors, heated by a further 10-100° K, preferably 20-50° K, above the vaporization temperature of the XDA under the prevailing pressure, are reacted with phosgene by known methods of gas-phase phosgenation.

Figure 1:
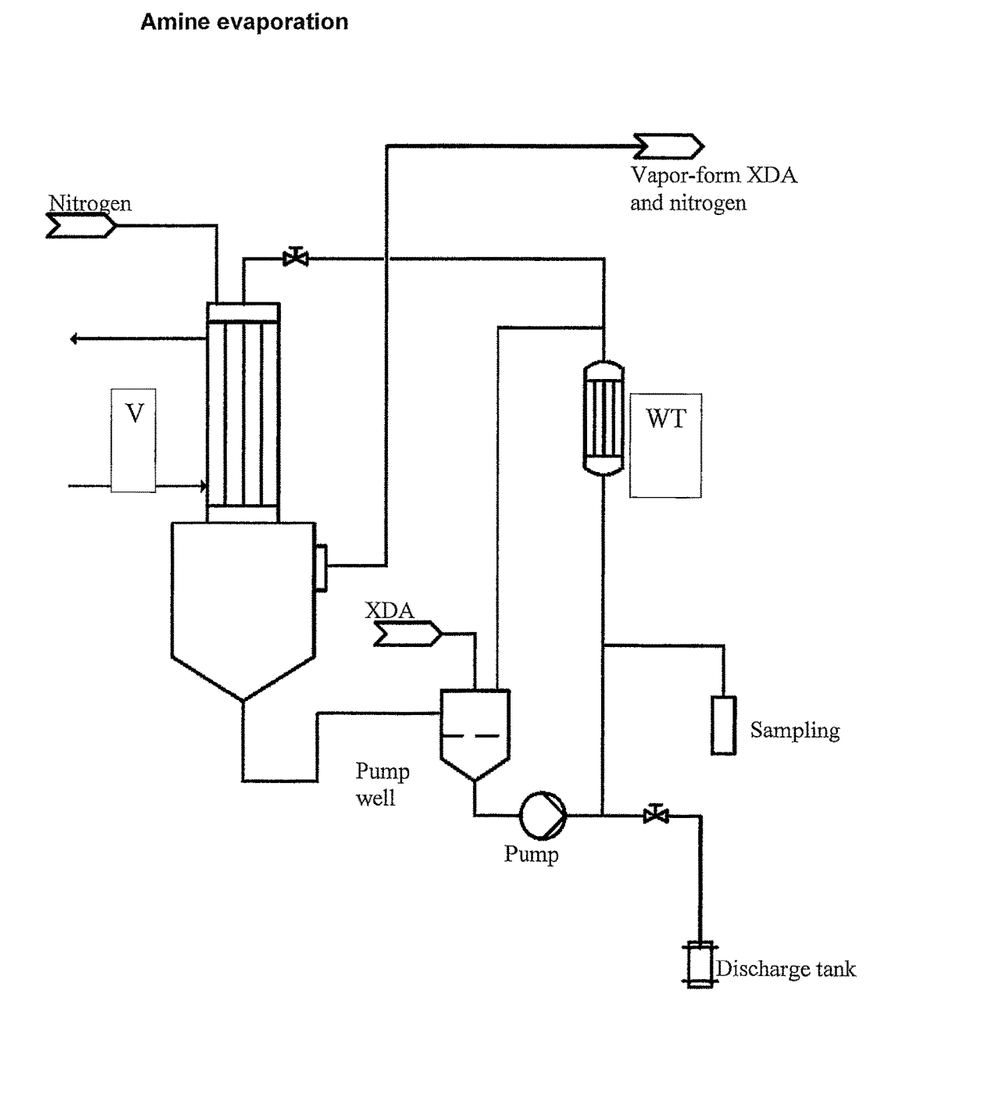
FIG. 1 shows a schematic of a plant for gas-phase phosgenation with an amine evaporation stage.

In the method of the invention, XDA, optionally with addition of an inert gas such as nitrogen, for example, is vaporized at a pressure <1000 mbar abs. in a vaporizer, and for example in a downpipe devolatilizer. The holdup in the vaporizer circuit here is calculated, via the sizing of the apparatus and pipelines and by the vaporizer rate, to be such that the mean residence time is situated in the range of the values indicated above. By cooling of the hot recycle stream of unvaporized XDA from the vaporizer (V) by means of a heat exchanger (WT), the temperature in the pumping circuit of the vaporization is set in such a way as to be neither below nor above the values indicated above. One possible embodiment of the amine evaporation of the invention is shown in FIG. 1.

In one preferred embodiment, the XDA is admixed prior to the vaporization with one or more stabilizers in concentrations of 50-2000 ppm (ppm by weight), preferably 100-1000 ppm, more preferably 200-500 ppm, based on XDA.

Suitable stabilizers are, for example, antioxidants, examples being sterically hindered phenols such as 2,6-di-tert-butyl-p-cresol (Ionol) and its derivatives, acids, examples being alkyl-substituted benzosulfonic acids such as toluenesulfonic acids, sulfonamides such as p-toluenesulfonamide, phosphites, and secondary aromatic amines. Preferred stabilizers are those having a much higher boiling point than XDA, which therefore remain in the pumping circuit. Preferred stabilizers are sterically hindered phenols. An example of a preferred stabilizer is TINUVIN 571 from BASF.

In spite of these measures, there may be an accumulation of nonvolatile xylylene-polyamines in the vaporizer circuit. It may therefore be advantageous, by extracting a certain quantity of XDA from the vaporizer circuit, to limit its concentration to a level such that the amine vaporization is not adversely affected, by an increase in boiling point, for example. The extraction rate is therefore calculated to be such that the concentration of xylylene-polyamines in the vaporizer circuit is <10%, preferably <5%.

Alternatively for the vaporization it is of course also possible to use other types of vaporizer which allow the extraction of certain quantities of nonvolatile components, examples being thin-film evaporators or flash vaporizers.

The inert gas to be added optionally before or after the vaporization to the XDA is selected from the group encompassing He, Ne, Ar, and preferably $N_2$. Moreover, the vapors of an inert solvent such as xylene, o-dichlorobenzene (ODB) or, preferably, monochlorobenzene (MCB), for example, may also be added to the amine for dilution. The amount of any inert gas or solvent vapor used as diluent is not critical, but can be utilized in order to lower the vaporization temperature of the amine.

Before being mixed with the phosgene, the gaseous, optionally diluted XDA is heated by a further 10-100° K, preferably 20-50° K, above the temperature which is needed in the pumping circuit for the vaporization of the XDA under the pressure prevailing there. Here, in one preferred embodiment of the method, droplet separators are installed between the vaporization and superheating systems, and/or the vaporization and superheating apparatus also possesses the function of a droplet separator. Suitable droplet separators are described for example in "Droplet Separation", A. Bürkholz, VCH Verlagsgesellschaft Weinheim—New York—Basel—Cambridge 1989. Preferred droplet separators are those giving rise to a low level of pressure loss. With particular preference the vaporized XDA is brought via an afterheater to the desired feed temperature, the afterheater also functioning as droplet separator. Very preferably this afterheater has a liquid drain, in order to ensure the continual emptying of the separator. The production of a superheated XDA stream which is substantially droplet-free before entry into the reactor significantly increases the reactor run time.

Before being fed into the reactor, the phosgene used is heated to a temperature of 200-450° C., preferably 250-350° C. The optionally diluted, superheated reactant streams are passed into a cylindrical reaction space, where they are mixed with one another and reacted. During the exothermic phosgenating reaction, a turbulent flow is maintained.

The volume flow rates of gaseous XDA and phosgene are selected such that the molar phosgene excess based on one amino group is 30% to 300%, preferably 60% to 200%.

Examples of suitable cylindrical reaction spaces are tubular reactors without internals and without moving parts in the interior of the reactor. The tubular reactors consist generally of steel, glass, alloyed or enameled steel, and are dimensioned such as to enable complete reaction of the XDA with the phosgene under the process conditions. The gas streams are generally introduced into the tubular reactor at one end thereof, it being possible for this introduction to take place for example through nozzles mounted at that end of the tubular reactor, or through a combination of nozzle and an annular gap between nozzle and mixing tube. The mixing tube is likewise held at a temperature within the range from 200 to 450° C., preferably 250 to 350° C., this temperature optionally being maintained by heating of the reaction tube.

When the method of the invention is being carried out, the pressure in the feed lines to the reaction space is generally <1000 mbar abs., preferably 350 to 900 mbar abs., more preferably 500 to 800 mbar abs., and the pressure at the exit from the reaction space is generally <950 mbar abs., preferably 300 to 850 mbar abs., more preferably 450 to 750 mbar abs.; by maintaining a suitable differential pressure, a flow rate within the reaction space of 3 to 100, preferably 5 to 75, and more preferably 10 to 60 m/s is maintained. Under these conditions, turbulent flow conditions generally prevail within the reaction space.

The residence time of the reaction mixture in the reactor is 0.1 to 2 s, preferably 0.2 to 1 s, and very preferably 0.4 to 0.8 s. The residence time is calculated from the temporal throughput of the reactant streams, the reactor dimensioning, and the reaction parameters of pressure and temperature.

After the phosgenation reaction has taken place in the reaction space, the gaseous mixture continually leaving the reaction space is freed from the isocyanate formed. This can be done, for example, by means of an inert solvent, whose temperature is selected such that on the one hand it is above the decomposition temperature of the carbamoyl chloride corresponding to the isocyanate, and on the other hand is below the condensation temperature of the isocyanate and preferably also of the solvent optionally used as diluent in the vapor form, causing isocyanate and auxiliary solvent to condense and dissolve in the solvent, while excess phosgene, hydrogen chloride, and any inert gas used as diluent pass through the condensation stage or the solvent in gaseous form. For the selective recovery of the isocyanate from the mixture leaving the reaction space in gaseous form especially suitable solvents are those of the type exemplified above that are held at a temperature of 60 to 200° C., preferably 90 to 170° C., more particularly technical mono- (MCB) and dichlorobenzene (ODB). Methods that may be thought of for selective condensation of the resulting isocyanate from the gas mixture leaving the reactor, using solvents of this kind, are, for example, the passing of the gas mixture through the stated solvent, or the jetting of the solvent (solvent mist) into the gas stream, and quenches.

The gas mixture passing through the condensation stage for the recovery of the isocyanate is subsequently freed in a conventional way from excess phosgene. This may be done by means of a cold trap, by absorption in an inert solvent held at a temperature of −10° C. to 8° C. (e.g., chlorobenzene, MCB, or dichlorobenzene, ODB), or by adsorption and hydrolysis of activated carbon. The hydrogen chloride gas passing through the phosgene recovery stage may be recycled in a conventional way for the recovery of the chlorine, which is needed for the phosgene synthesis.

The isocyanates are prepared in pure form preferably by distillative workup of the isocyanate solution in the solvent used for the isocyanate condensation.

The invention further relates to 1,3- and/or 1,4-xylylene diisocyanate produced or producible by the method of the invention. The two aforementioned compounds differ from 1,3- and/or 1,4-xylylene diisocyanate which has been generated via the liquid-phase phosgenation of XDA, as employed to date. This is clear in particular from the fact that when 1,3- and/or 1,4-xylylene diisocyanate generated in accordance with the invention is used in a polythiourethane formulation, the polythiourethane moldings obtained after polymerization with a polythiol component have a much lower hazing tendency relative to moldings generated from the same polythiourethane formulation, but with 1,3- and/or 1,4-xylylene diisocyanate from the liquid-phase phosgenation.

Furthermore, the method of the invention also affords process-engineering advantages. In order to satisfy the exacting requirements associated with optical applications, laborious processes have to date been needed for the preparation of the raw materials. EP-A 1 908 749, for instance, describes a process for producing XDI that involves first preparing the hydrochloride with the XDA and then subjecting it to phosgenation under elevated pressure in order to obtain grades of appropriate purity. With the method of the invention, in contrast, the XDA is phosgenated directly.

In line with the implementation above, a further subject of the present invention is the use of 1,3- and/or 1,4-xylylene diisocyanate produced in accordance with the invention for producing transparent polyurethanes or polythiourethanes, especially for producing transparent polyurethane or polythiourethane moldings, the polythiourethane moldings being particularly preferred on account of their good optical properties.

In the context of the present invention, the term "transparent" is understood to mean that the transparent body has a transmittance of ≥85% at a thickness of 2 mm with the standard illuminant D65 (defined in DIN 6173). In the case of the optional accompanying use of UV stabilizers and dyes, this transmittance FIGURE may deviate from the above-stated FIGURE of ≥85%.

The invention, moreover, also relates to the polyurethane or polythiourethane moldings themselves that are produced in accordance with the invention, with the polythiourethane moldings being particularly preferred on account of their good optical properties.

A suitable composition for producing transparent polythiourethanes or polythiourethane bodies may comprise or consist of
A) a polyisocyanate component comprising or based on 1,3- and/or 1,4-xylylene diisocyanate (XDI) produced or producible via gas-phase phosgenation in accordance with the present invention, and also, if desired, at least one further polyisocyanate having an isocyanate-group functionality of at least 2 per molecule,
B) a thiol component comprising or consisting of at least one polythiol having a thiol-group functionality of at least 2 per molecule,
and also, optionally,
C) auxiliaries and additives,
the ratio of isocyanate groups to isocyanate-reactive groups being 0.5:1 to 2.0:1.

"Based on" in the present context means that the polyisocyanate component may also include prepolymers produced from the 1,3- and/or 1,4-xylylene diisocyanate (XDI) generated in accordance with the invention.

A suitable composition for producing transparent polyurethanes or polyurethane bodies may comprise or consist of
A) a polyisocyanate component comprising or based on 1,3- and/or 1,4-xylylene diisocyanate (XDI) produced or producible via gas-phase phosgenation in accordance with the present invention, and also, if desired, at least one further polyisocyanate having an isocyanate-group functionality of at least 2 per molecule,
B) a polyol component comprising or consisting of at least one polyol having a hydroxyl-group functionality of at least 2 per molecule,
and also, optionally,
C) auxiliaries and additives,
the ratio of isocyanate groups to isocyanate-reactive groups being 0.5:1 to 15.0:1, preferably 0.5:1 to 2.0:1.

Systems with a mixture of polyol component and thiol component are also within the scope of the present invention.

The polyisocyanate component A) may also comprise further polyisocyanates. In principle, further polyisocyanates which can be used in the context of the present invention are all polyisocyanates known per se. These are, for example, those from the 140 to 400 g/mol molecular weight range, such as, for example, 1,4-diisocyanatobutane, 1,5-diisocyanatopentane, 1,6-diisocyanatohexane (HDI), 1,5-diisocyanato-2,2-dimethylpentane, 2,2,4- and/or 2,4,4-trimethyl-1,6-diisocyanatohexane, 1,8-diisocyanatooctane, 1,9-diisocyanatononane, 1,10-diisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methyl-cyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane (H12-MDI), 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyl-dicyclohexylmethane, 4,4'-diisocyanato-1,1'-bi(cyclohexyl), 2,5-bis(isocyanatomethyl)-bicyclo[2.2.1]heptane, 2,6-bis(isocyanatomethyl)bicyclo[2.2.1]heptane, 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(1-isocyanato-1-methylethyl)benzene (TMXDI), bis(4-(1-isocyanato-1-methylethyl)phenyl) carbonate, 1,3- and 1,4-phenylene diisocyanate, 2,4- and 2,6-tolylene diisocyanate, and any desired mixtures of these isomers, diphenylmethane 2,4'- and/or -4,4'-diisocyanate and naphthylene 1,5-diisocyanate, and also any desired mixtures of such diisocyanates. These isocyanates may have been generated by any desired operations.

As further polyisocyanate it is likewise possible to use, generated via liquid-phase phosgenation, 1,3-bis(isocyanatomethyl)benzene (m-xylylene diisocyanate, m-XDI), 1,4-bis(isocyanatomethyl)benzene (p-xylylene diisocyanate, p-XDI).

Where the composition according to the invention comprises further polyisocyanates as well as the inventively generated 1,3- and/or 1,4-xylylene diisocyanate, the polyisocyanate component consists to an extent of at least 80 wt %, based on the polyisocyanate component, of polyisocyanate produced by gas-phase phosgenation, more particularly to an extent of at least 85 wt %, more preferably at least 90 wt %, very preferably at least 95 wt %, or even at least 96 or at least 98 wt %.

The composition of the invention for producing polythiourethane moldings further comprises a thiol component B). This component comprises or consists of at least one polythiol having a thiol-group functionality of at least two per molecule, more particularly of 2 to 6, preferably 2 to 4, more preferably of 3 to 4. Here it is also possible to use mixtures of polythiols with different functionalities, resulting in uneven average functionalities. A polythiol for the purposes of the present invention refers to organic thiols having two or more thiol groups. The syllable "poly" relates essentially to the number of thiol groups and does not necessarily mean that the polythiol must have an oligomeric or even polymeric structure. Nevertheless, the polythiols used in accordance with the invention may well also possess a polyether framework, a polythiol ether framework, or a mixed framework made up of O-ether and S-ether units.

The polythiol may have an average molecular weight of 80 (methanedithiol) up to about 12 000 g/mol, preferably 250 to 8000 g/mol.

Examples of suitable polythiols include methanedithiol, 1,2-ethanedithiol, 1,1-propanedithiol, 1,2-propanedithiol, 1,3-propanedithiol, 2,2-propanedithiol, 1,4-butanedithiol, 2,3-butanedithiol, 1,5-pentanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, and 2-methylcyclohexane-2,3-dithiol, polythiols containing thioether groups, such as 2,4-dimercaptomethyl-1,5-dimercapto-3-thiapentane, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 4,5-bis(mercaptoethylthio)-1,10-dimercapto-3,8-dithiadecane, tetrakis(mercaptomethyl)methane, 1,1,3,3-tetrakis(mercapto-methylthio)propane, 1,1,5,5-tetrakis(mercaptomethylthio)-3-thiapentane, 1,1,6,6-tetrakis(mercaptomethylthio)-3,4-dithiahexane, 2-mercaptoethylthio-1,3-dimercaptopropane, 2,3-bis(mercaptoethylthio)-1-mercaptopropane, 2,2-bis(mercaptomethyl)-1,3-dimercaptopropane, bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptopropyl) disulfide, bis(mercaptomethylthio)methane, tris(mercaptomethylthio)methane, bis(mercaptoethylthio)methane, tris(mercaptoethylthio)methane, bis(mercaptopropylthio)methane, 1,2-bis(mercaptomethylthio)ethane, 1,2-bis(mercaptoethylthio)ethane, 2-mercaptoethylthio)ethane, 1,3-bis(mercaptomethylthio)propane, 1,3-bis(mercaptopropylthio)propane, 1,2,3-tris(mercaptomethylthio)propane, 1,2,3-tris(mercaptoethylthio)propane, 1,2,3-tris(mercaptopropylthio)propane, tetrakis(mercaptomethylthio)methane, tetrakis(mercaptoethylthiomethyl)methane, tetrakis(mercaptopropylthiomethyl)methane, 2,5-dimercapto-1,4-dithiane, 2,5-bis(mercaptomethyl)-1,4-dithiane and its oligomers obtainable according to JP-A 07118263, 1,5-bis(mercaptopropyl)-1,4-dithiane, 1,5-bis(2-mercaptoethylthiomethyl)-1,4-dithiane, 2-mercaptomethyl-6-mercapto-1,4-dithiacycloheptane, 2,4,6-trimercapto-1,3,5-trithiane, 2,4,6-trimercaptomethyl-1,3,5-trithiane and 2-(3-bis(mercaptomethyl)-2-thiapropyl)-1,3-dithiolane,
polyesterthiols, such as, for example, ethylene glycol bis(2-mercaptoacetate), ethylene glycol bis(3-mercaptopropionate), diethylene glycol 2-mercaptoacetate, diethylene glycol 3-mercaptopropionate, 2,3-dimercapto-1-propanol 3-mercaptopropionate, 3-mercapto-1,2-propanediol bis(2-mercaptoacetate), 3-mercapto-1,2-propanediol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), glycerol tris(2-mercaptoacetate), glycerol tris(3-mercaptopropionate), 1,4-cyclohexanediol bis(2-mercaptoacetate), 1,4-cyclohexanediol bis(3-mercaptopropionate), hydroxymethyl sulfide bis(2-mercaptoacetate), hydroxymethyl sulfide bis(3-mercaptopropionate), hydroxyethyl sulfide 2-mercaptoacetate, hydroxyethyl sulfide 3-mercaptopropionate, hydroxymethyl disulfide 2-mercaptoacetate, hydroxymethyl disulfide 3-mercaptopropionate, 2-mercaptoethyl ester thioglycolate and bis(2-mercaptoethylester) thiodipropionate, and also aromatic thio compounds, such as, for example, 1,2-dimercaptobenzene, 1,3-dimercaptobenzene, 1,4-dimercaptobenzene, 1,2-bis(mercaptomethyl)benzene, 1,4-bis(mercaptomethyl)benzene, 1,2-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,3,5-tris(mercaptoethyl)benzene, 1,2,4-tris(mercaptoethyl)benzene, 2,5-toluenedithiol, 3,4-toluenedithiol, 1,4-naphthalenedithiol, 1,5-naphthalenedithiol, 2,6-naphthalenedithiol, 2,7-naphthalenedithiol, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercapto-ethyl)benzene, 2,2'-dimercaptobiphenyl, and 4,4'-dimercaptobiphenyl.

Preferably the polythiol is selected from 4-mercaptomethyl-1,8-dimercapto-3,6-dithiaoctane, 2,5-bismercaptomethyl-1,4-dithiane, 1,1,3,3-tetrakis(mercaptomethylthio)propane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, trimethylolpropane tris(3-mercaptopropionate), trimethylolethane tris(2-mercaptoacetate), pentaerythritol tetrakis(2-mercaptoacetate) and/or pentaerythritol tetrakis(3-mercaptopropionate).

Aside from the thiol component B), the composition of the invention may also comprise other components which customarily react with polyisocyanates. Such components are, in particular, the customary polyether polyols, polyester polyols, polyetherpolyester polyols, polythioether polyols, polymer-modified polyether polyols, graft polyether polyols, polyether polyamines, hydroxyl-containing polyacetals and/or hydroxyl-containing aliphatic polycarbonates which are known from polyurethane chemistry, which customarily have a molecular weight of 106 to 12 000 g/mol, preferably 250 to 8000 g/mol. A broad overview of suitable coreactants B) is found for example in N. Adam et al.: "Polyurethanes", Ullmann's Encyclopedia of Industrial Chemistry, Electronic Release, 7th ed., chap. 3.2-3.4, Wiley-VCH, Weinheim 2005.

These polyols can be used in combination with, but preferably not together with a thiol component B), as polyol component B) in the aforementioned compositions for producing polyurethane moldings.

A polythiourethane in the sense of the present invention refers to a polymer in which more than half through all of the bonds between the polyisocyanate and the isocyanate-reactive component or components are thiourethane groups. There may therefore be other bonds present to an extent of less than half, such as urethane bridges or urea bridges, for example. In that case the composition of the invention further comprises other isocyanate-reactive component(s). These merely optional components are described in more detail below.

Suitable polyether polyols, where used, are for example those of the type specified in DE-A 2 622 951, column 6, line 65-column 7, line 47, or in EP-A 0 978 523 page 4, line 45 to page 5, line 14, provided they meet the above-specified functionality and molecular weight requirements. Particularly preferred polyether polyols B) are adducts of ethylene oxide and/or propylene oxide with glycerol, trimethylolpropane, ethylenediamine and/or pentaerythritol.

Suitable polyester polyols, where used, are for example those of the type specified in EP-A 0 978 523 page 5, lines 17 to 47 or in EP-A 0 659 792 page 6, lines 8 to 19, provided they meet the specifications given above, preferably polyols whose hydroxyl number is from 20 to 650 mg KOH/g.

Suitable polyacetal polyols, where used, are for example the known reaction products of simple glycols, such as diethylene glycol, triethylene glycol, 4,4'-dioxethoxydiphenyldimethylmethane (adduct of 2 mol of ethylene oxide with bisphenol A) or hexanediol, with formaldehyde, or else polyacetals prepared by polycondensation of cyclic acetals, such as trioxane, for example.

Amino polyethers or mixtures of amino polyethers may likewise be suitable, these thus being polyethers having groups that are reactive toward isocyanate groups and are composed to an extent of at least 50 equivalent %, preferably at least 80 equivalent %, of primary and/or secondary, aromatically or aliphatically bonded amino groups, and for the remainder, of primary and/or secondary, aliphatically bonded hydroxyl groups. Suitable such amino polyethers are for example the compounds specified in EP-A 0 081 701, column 4, line 26 to column 5, line 40. Likewise suitable as starting component E) are amino-functional polyetherurethanes or -ureas, as may be prepared, for example, by the method of DE-A 2 948 419, by hydrolysis of isocyanate-functional polyether prepolymers, or else polyesters that contain amino groups, from the above-specified molecular weight range.

Further suitable components reactive toward isocyanate groups are also, for example, the specific polyols described in EP-A 0 689 556 and EP-A 0 937 110, obtainable for example by reaction of epoxidized fatty acid esters with aliphatic or aromatic polyols with opening of the epoxide ring.

Polybutadienes containing hydroxyl groups may also optionally be used.

Furthermore, suitable components reactive toward isocyanate groups also include hydroxyl compounds containing sulfur. Examples here include simple mercaptoalcohols, such as 2-mercaptoethanol, 3-mercaptopropanol, 1,3-dimercapto-2-propanol, 2,3-dimercaptopropanol, and dithioerythritol, for example, alcohols containing thioether structures, such as di(2-hydroxyethyl) sulfide, 1,2-bis(2-hydroxyethylmercapto)ethane, bis(2-hydroxyethyl) disulfide, and 1,4-dithiane-2,5-diol, for example, or sulfur-containing diols with a polyesterurethane, polythioesterurethane, polyesterthiourethane or polythioesterthiourethane structure of the type specified in EP-A 1 640 394.

Other isocyanate-reactive compounds which the compositions of the invention may comprise include hydroxy- and/or amino-functional components of low molecular weight, in other words those from a molecular weight range from 60 to 500 g/mol, preferably from 62 to 400 g/mol.

These are, for example, simple mono- or polyhydric alcohols having 2 to 14, preferably 4 to 10 carbon atoms, such as, for example, 1,2-ethanediol, 1,2- and 1,3-propanediol, the isomeric butanediols, pentanediols, hexanediols, heptanediols, and octanediols, 1,10-decanediol, 1,2- and 1,4-cyclohexanediol, 1,4-cyclohexanedimethanol, 4,4'-(1-methylethylidene)biscyclohexanol, 1,2,3-propanetriol, 1,1,1-trimethylolethane, 1,2,6-hexanetriol, 1,1,1-trimethylolpropane, 2,2-bis(hydroxymethyl)-1,3-propanediol, bis(2-hydroxyethyl)hydroquinone, 1,2,4- and 1,3,5-trihydroxycyclohexane, or 1,3,5-tris(2-hydroxyethyl) isocyanurate.

Examples of suitable amino-functional compounds of low molecular weight are aliphatic and cycloaliphatic amines and amino alcohols having amino groups with primary and/or secondary attachment, such as, for example, cyclohexylamine, 2-methyl-1,5-pentanediamine, diethanolamine, monoethanolamine, propylamine, butylamine, dibutylamine, hexylamine, monoisopropanolamine, diisopropanolamine, ethylenediamine, 1,3-diaminopropane, 1,4-diaminobutane, isophoronediamine, diethylenetriamine, ethanolamine, aminoethylethanolamine, diaminocyclohexane, hexamethylenediamine, methyliminobispropylamine, iminobispropylamine, bis(aminopropyl)piperazine, aminoethylpiperazine, 1,2-diaminocyclohexane, triethylenetetramine, tetraethylenepentamine, 1,8-p-diaminomenthane, bis(4-aminocyclohexyl)methane, bis(4-amino-3-methylcyclohexyl)methane, bis(4-amino-3,5-dimethylcyclohexyl)methane, bis(4-amino-2,3,5-trimethylcyclohexyl)methane, 1,1-bis(4-aminocyclohexyl) propane, 2,2-bis(4-aminocyclohexyl)propane, 1,1-bis(4-aminocyclohexyl)ethane, 1,1-bis(4-aminocyclohexyl) butane, 2,2-bis(4-aminocyclohexyl)butane, 1,1-bis(4-amino-3-methylcyclohexyl)ethane, 2,2-bis(4-amino-3-methylcyclohexyl)propane, 1,1-bis(4-amino-3,5-dimethylcyclohexyl)ethane, 2,2-bis(4-amino-3,5-dimethylcyclohexyl)propane, 2,2-bis(4-amino-3,5-dimethyl-cyclohexyl)butane, 2,4-diaminodicyclohexylmethane, 4-aminocyclohexyl-4-amino-3-methylcyclohexylmethane, 4-amino-3,5-dimethylcyclohexyl-4-amino-3-methylcyclohexylmethane, and 2-(4-aminocyclohexyl)-2-(4-amino-3-methylcyclohexyl)methane.

Examples of aromatic polyamines, especially diamines, having molecular weights below 500 g/mol, which represent suitable isocyanate-reactive compounds B), are, for example, 1,2- and 1,4-diaminobenzene, 2,4- and 2,6-diaminotoluene, 2,4'- and/or 4,4'-diaminodiphenylmethane, 1,5-diaminonaphthalene, 4,4',4''-triaminotriphenylmethane, 4,4'-bis(methyl-amino)diphenylmethane or 1-methyl-2-methylamino-4-aminobenzene. 1-Methyl-3,5-diethyl-2,4-diaminobenzene, 1-methyl-3,5-diethyl-2,6-diaminobenzene, 1,3,5-trimethyl-2,4-diaminobenzene, 1,3,5-triethyl-2,4-diaminobenzene, 3,5,3',5'-tetraethyl-4,4'-diaminodiphenylmethane, 3,5,3',5'-tetraisopropyl-4,4'-diaminodiphenylmethane, 3,5-diethyl-3',5'-diisopropyl-4,4'-diaminodiphenylmethane, 3,3'-diethyl-5,5'-diisopropyl-4,4'-diaminodiphenylmethane, 1-methyl-2,6-diamino-3-isopropylbenzene, liquid mixtures of polyphenyl polymethylene polyamines, of the kind obtainable in a known way by condensation of aniline with formaldehyde, and also any desired mixtures of such polyamines. Particular mention may be made in this context, for example of mixtures of 1-methyl-3,5-diethyl-2,4-diaminobenzene with 1-methyl-3,5-diethyl-2,6-diaminobenzene in a weight ratio of 50:50 to 85:15, preferably of 65:35 to 80:20.

The use of amino-functional polyethers of low molecular weight, having molecular weights below 500 g/mol, is likewise possible. These are, for example, those having primary and/or secondary, aromatically or aliphatically bonded amino groups, whose amino groups are attached optionally via urethane groups or ester groups to the polyether chains, and which are obtainable in accordance with known methods already described above for the preparation of the amino polyethers of higher molecular weight.

Optionally it is also possible for sterically hindered aliphatic diamines having two amino groups with secondary attachment to be used as components reactive toward isocyanate groups, such as, for example, the reaction products, known from EP-A 0 403 921, of aliphatic and/or cycloaliphatic diamines with maleic or fumaric esters, or the hydrogenation products, described in DE-A 19 701 835, for example, of Schiff bases obtainable from aliphatic and/or cycloaliphatic diamines and ketones, such as diisopropyl ketone, for example.

Besides the stated starting components A) and B), there may additionally be used, optionally, auxiliaries and additives C), such as, for example, catalysts, surface-active agents, UV stabilizers, antioxidants, fragrances, mold release agents, fillers and/or pigments.

For accelerating reaction it is possible for example for customary catalysts known from polyurethane chemistry to be employed. Examples here include tertiary amines, such as triethylamine, tributylamine, dimethylbenzylamine, diethylbenzylamine, pyridine, methylpyridine, dicyclohexylmethylamine, dimethylcyclohexylamine, N,N,N',N'-tetramethyl-diaminodiethyl ether, bis(dimethylaminopropyl)urea, N-methyl- and N-ethylmorpholine, N-cocomorpholine, N-cyclohexylmorpholine, N,N,N',N'-tetramethylethylenediamine, N,N,N',N'-tetramethyl-1,3-butanediamine, N,N,N',N'-tetramethyl-1,6-hexanediamine, pentamethyldiethylenetriamine, N-methylpiperidine, N-dimethylaminoethylpiperidine, N,N'-dimethylpiperazine, N-methyl-N'-dimethyl-aminopiperazine, 1,8-diazabicyclo[5.4.0]undec-7-ene (DBU), 1,2-dimethylimidazole, 2-methylimidazole, N,N-dimethylimidazole-β-phenylethyl-amine, 1,4-diazabicyclo-[2.2.2]octane, bis(N,N-dimethyl-aminoethyl) adipate; alkanolamine compounds, such as, for example, triethanolamine, triisopropanolamine, N-methyl- and N-ethyl-diethanolamine, dimethyl-aminoethanol, 2-(N,N-dimethylaminoethoxy)ethanol, N,N',N"-tris(dialkylaminoalkyl)hexahydrotriazines, as for example N,N',N"-tris(dimethylaminopropyl)-s-hexahydrotriazine and/or bis(dimethylaminoethyl) ether; metal salts, such as, for example, inorganic and/or organic compounds of iron, of lead, of bismuth, of zinc, and/or of tin in customary oxidation states of the metal, examples being iron(II) chloride, iron(III) chloride, bismuth(III) bismuth(III) 2-ethylhexanoate, bismuth(III) octoate, bismuth(III) neodecanoate, zinc chloride, zinc 2-ethylcaproate, tin(II) octoate, tin(II) ethylcaproate, tin(II) palmitate, dibutyltin(IV) dilaurate (DBTL), dibutyltin(IV) dichloride, dimethyltin(IV) dichloride, or lead octoate; amidines, such as, for example, 2,3-dimethyl-3,4,5,6-tetrahydropyrimidine; tetraalkylammonium hydroxides, such as, for example, tetramethyl-ammonium hydroxide; alkali metal hydroxides, such as, for example, sodium hydroxide and alkali metal alkoxides, such as sodium methoxide and potassium isopropoxide, for example, and also alkali metal salts of long-chain fatty acids having 10 to 20 C atoms and optionally pendant OH groups.

Preferred catalysts C) for use are tertiary amines, bismuth compounds and tin compounds of the type stated.

In the production of the lightfast polyurethane, polythiourethane and/or polyurea compositions of the invention, the catalysts exemplified may be used individually or in the form of any desired mixtures with one another, and are employed optionally in amounts of 0.001 to 5.0 wt %, preferably 0.002 to 2 wt %, calculated as total amount of catalysts used, based on the total amount of the starting compounds used.

In accordance with the method of the invention, preference is given to producing compact transparent shaped parts of high refractive index. By addition of suitable blowing agents it is possible, if desired, to obtain foamed moldings as well, however. Examples of blowing agents suitable for this purpose include highly volatile organic substances, such as, for example acetone, ethyl acetate, halogen-substituted alkanes, such as methylene chloride, chloroform, ethylidene chloride, vinylidene chloride, monofluorotrichloromethane, chlorotrifluoromethane or dichlorodifluoromethane, butane, hexane, heptane or diethyl ether and/or dissolved inert gases, such as nitrogen, air or carbon dioxide, for example.

Examples of chemical blowing agents C) that are contemplated, these being blowing agents that form gaseous products by virtue of reaction, with isocyanate groups, for example, include water, compounds containing water of hydration, carboxylic acids, tertiary alcohols, e.g., tert-butanol, carbamates, examples being the carbamates described in EP-A 1 000 955, especially at page 2, lines 5 to 31 and page 3, lines 21 to 42, carbonates, examples being ammonium carbonate and/or ammonium hydrogencarbonate and/or guanidine carbamate.

A blowing effect may also be achieved by adding compounds—azo compounds, for example—which decompose at temperatures above room temperature and, in so doing, give off gases, such as nitrogen, for example. Further examples of blowing agents, and also details concerning the use of blowing agents, are described in Kunststoff-Handbuch, volume VII, edited by Vieweg and Höchtlen, Carl-Hanser-Verlag, Munich 1966, e.g., at pages 108 and 109, 453 to 455, and 507 to 510.

In accordance with the invention it is also possible for surface-active additives C) to be used accompanyingly as emulsifiers and foam stabilizers. Examples of suitable emulsifiers are the sodium salts of castor oil sulfonates or fatty acids, salts of fatty acids with amines, such as diethylamine oleate or diethanolamine stearate, for example. Alkali metal salts or ammonium salts of sulfonic acids, such as of dodecylbenzenesulfonic acids, of fatty acids, such as ricinoleic acid, or of polymeric fatty acids, or ethoxylated nonylphenol, can also be used accompanyingly as surface-active additives.

The abovementioned emulsifiers and stabilizers for optional accompanying use in the method of the invention may be employed either individually or else in any desired combinations with one another.

The bodies obtained from the polyurethane materials usable and/or producible in accordance with the invention are already distinguished as they are by very good light stability, in other words even without addition of corresponding stabilizers. Nevertheless, in the course of their production, UV protectants (light stabilizers) or antioxidants of the known kind may additionally be used as further auxiliaries and additives C).

Examples of suitable UV stabilizers C) are piperidine derivatives, such as, for example, 4-benzoyloxy-2,2,6,6-tetramethylpiperidine, 4-benzoyloxy-1,2,2,6,6-pentamethylpiperidine, bis(2,2,6,6-tetramethyl-4-piperidyl) sebacate, bis(1,2,2,6,6-pentamethyl-4-piperidyl) sebacate, methyl 1,2,2,6,6-pentamethyl-4-piperidyl sebacate, bis(2,2,6,6-tetramethyl-4-piperidyl) suberate or bis(2,2,6,6-tetramethyl-4-piperidyl) dodecanedioate, benzophenone derivatives, such as, for example, 2,4-dihydroxy-, 2-hydroxy-4-methoxy-, 2-hydroxy-4-octoxy-, 2-hydroxy-4-dodecyloxy- or 2,2'-dihydroxy-4-dodecyloxy-benzophenone, benzotriazol derivatives, such as, for example, 2-(5-methyl-2-hydroxyphenyl)benzotriazole, 2-(5-tert-butyl-2-hydroxyphenyl)benzotriazole, 2-(5-tert-octyl-2-hydroxyphenyl)-benzotriazole, 2-(5-dodecyl-2-hydroxyphenyl) benzotriazole, 2-(3,5-di-tert-butyl-2-hydroxyphenyl)-5-chlorobenzotriazole, 2-(3,5-di-tert-amyl-2-hydroxyphenyl) benzotriazole, 2-(3,5-di-tert-butyl-2-hydroxy-phenyl) benzotriazole, 2-(3-tert-butyl-5-methyl-2-hydroxyphenyl)-

5-chlorobenzotriazole, and esterification products of 2-(3-tert-butyl-5-propionyl-2-hydroxyphenyl)benzotriazole with polyethylene glycol 300, oxalanilides, such as 2-ethyl-2'-ethoxy- or 4-methyl-4'-methoxyoxalanilide, salicylic esters, such as, for example, phenyl salicylate, 4-tert-butylphenyl salicylate, and 4-tert-octylphenyl salicylate, cinnamic ester derivatives, such as, for example, methyl α-cyano-β-methyl-4-methoxycinnamate, butyl α-cyano-β-methyl-4-methoxycinnamate, ethyl α-cyano-β-phenylcinnamate, and isooctyl α-cyano-β-phenylcinnamate, or malonic ester derivatives, such as, for example, dimethyl 4-methoxybenzylidenemalonate, diethyl 4-methoxybenzylidenemalonate, and dimethyl 4-butoxybenzyl-idenemalonate. These light stabilizers may be employed either individually or else in any desired combinations with one another.

Examples of suitable antioxidants C) are the known sterically hindered phenols, such as, for example, 2,6-di-tert-butyl-4-methylphenol (lonol), pentaerythritol tetrakis(3-(3,5-di-tert-butyl-4-hydroxyphenyl)propionate), octadecyl 3-(3,5-di-tert-butyl-4-hydroxyphenyl)-propionate, triethylene glycol bis(3-tert-butyl-4-hydroxy-5-methylphenyl)propionate, 2,2'-thiobis(4-methyl-6-tert-butylphenol), 2,2'-thiodiethyl bis[3-(3,5-di-tert-butyl-4-hydroxyphenyl) propionate), which may be employed either individually or else in any desired combinations with one another.

Examples of further auxiliaries and additives C) for optional accompanying use are the known flame retardants, such as, for example, trischloroethyl phosphate, ammonium phosphate or ammonium polyphosphate, fillers, such as, for example, barium sulfate, kieselguhr, carbon black, whiting, or else glass fibers with reinforcing activity.

Lastly it is also possible optionally to use the conventional internal mold release agents, dyes, pigments, hydrolysis stabilizers, fungistatic substances, and substances with bacteriostatic effect.

With particular preference the composition of the invention comprises as component C) at least one mold release agent selected from mono- and/or dialkyl phosphates and/or mono- and/or dialkoxyalkyl phosphates. Mono- and/or dialkyl phosphates are, in particular, mono- and/or dialkyl phosphates having 2 to 18 carbon atoms in the alkyl radical, preferably 8 to 12 carbon atoms. Particularly preferred mono- and/or dialkoxyalkyl phosphates possess 2 to 12 carbon atoms in the alkoxyalkyl radical and up to three ether groups per alkoxyalkyl radical, with the aforementioned mono- and/or alkoxyalkyl phosphates having, in particular, 4 to 10 carbon atoms in the alkoxyalkyl radical. The preferred mono/dialkyl phosphates and mono/dialkoxyalkyl phosphates are particularly advantageous since in addition to their actual mold release agent function they additionally display a favorable influence over the reaction rate in the reaction of the polyisocyanate component with the thiol component, insofar as their addition reduces the reaction rate of the two components with one another. This results ultimately in moldings of higher optical quality, and in greater ease of handling of the composition after the components have been mixed.

Examples of suitable internal demolding agents are methyl phosphate, dimethyl phosphate, methoxyethyl phosphate, methoxypropyl phosphate, di(methoxyethyl) phosphate, methoxyethyl ethoxyethyl phosphate, methoxyethyl propoxyethyl phosphate, di(methoxypropyl) phosphate, ethyl phosphate, diethyl phosphate, ethoxyethyl phosphate, di(ethoxyethyl) phosphate, ethoxypropyl phosphate, ethoxyethyl propoxyethyl phosphate, di(ethoxypropyl) phosphate, ethoxyethyl butoxyethyl phosphate, isopropyl phosphate, diisopropyl phosphate, propoxyethyl phosphate, di(propoxyethyl) phosphate, propoxypropyl phosphate, di(propoxypropyl) phosphate, butyl phosphate, dibutyl phosphate, butoxyethyl phosphate, butoxypropyl phosphate, di(butoxyethyl) phosphate, pentoxyethyl phosphate, bis(2-ethylhexyl) phosphate, di(hexyloxyethyl) phosphate, octyl phosphate, dioctyl phosphate, decyl phosphate, isodecyl phosphate, diisodecyl phosphate, isodecyloxyethyl phosphate, di(decyloxyethyl) phosphate, dodecyl phosphate, didoceyl phosphate, tridecanole phosphate, bis(tridecanol) phosphate, stearyl phospate, distearyl phosphate, and any desired mixtures of such compounds.

The compositions of the invention, based on the overall composition, contain advantageously 0.002 to 4 wt % of mono/dialkyl phosphates and/or mono/dialkyl alkoxy phosphates, preferably 0.005 to 2 wt %. The aforesaid amounts for use are based on the total amount of these substances as mold release agents.

One particularly preferred composition of the invention for producing transparent polythiourethane bodies or transparent polythiourethane comprises or consists of A) 35 to 65 wt %, based on the composition, more particularly 45 to 55 wt %, of a polyisocyanate component comprising at least 70 to 99.8 wt %, more particularly 85 to 99.7 wt %, based on the polyisocyanate component, of 1,3- and/or 1,4-xylylene diisocyanate (XDI) generated via gas-phase phosgenation in accordance with the present invention, B) 35 to 65 wt %, based on the composition, more particularly 45 to 55 wt %, of a thiol component comprising at least one polythiol having a thiol-group functionality of at least 2 per molecule, the thiol component consisting more particularly of a polythiol having a thiol-group functionality of 3 per molecule, namely DMPT (4-mercaptomethyl-1,8-dimercapto-3,6-dithiaoctane), and also C) auxiliaries and additives comprising 0.002 to 4 wt %, more particularly 0.005 to 2 wt %, of a mold release agent selected from mono- and/or dialkyl phosphates having 2 to 18 carbon atoms in the alkyl radical and/or from mono- and/or dialkoxyalkyl phosphates having 2 to 12 carbon atoms in the alkoxyalkyl radical and up to three ether groups per alkoxyalkyl radical, the ratio of isocyanate groups to isocyanate-reactive groups being 0.5:1 to 2.0:1.

One particularly preferred composition of the invention for producing a transparent polyurethane or polyurethane body comprises or consists of A) 60 to 97 wt %, based on the composition, more particularly 80 to 95 wt %, of a polyisocyanate component comprising at least 70 to 99.8 wt %, more particularly 85 to 99.7 wt %, based on the polyisocyanate component, of 1,3- and/or 1,4-xylylene diisocyanate (XDI) generated via gas-phase phosgenation in accordance with the present invention, B) 3 to 40 wt %, based on the composition, more particularly 5 to 10 wt %, of a polyol component comprising or consisting of at least one polyol having a hydroxyl-group functionality of at least 2 per molecule, and also C) auxiliaries and additives comprising 0.002 to 4 wt %, more particularly 0.005 to 2 wt %, of a mold release agent selected from mono- and/or dialkyl phosphates having 2 to 18 carbon atoms in the alkyl radical and/or from mono- and/or dialkoxyalkyl phosphates having 2 to 12 carbon atoms in the alkoxyalkyl radical and up to three ether groups per alkoxyalkyl radical, preferably dibutyl phosphate, the ratio of isocyanate groups to isocyanate-reactive groups being 0.5:1 to 15.0:1, preferably 0.5:1 to 2.0:1.

A further subject of the present invention relates to a method for producing transparent polythiourethane bodies by reaction of a composition comprising or consisting of A) a polyisocyanate component comprising 1,3- and/or 1,4-xylylene diisocyanate (XDI) produced or producible via gas-phase phosgenation in accordance with the present invention, and also, if desired, at least one further polyisocyanate having an isocyanate-group functionality of at least 2 per molecule, B) a thiol component comprising or consisting of at least one polythiol having a thiol-group functionality of at least 2 per molecule, and also, optionally, C) further auxiliaries and additives, the ratio of isocyanate groups to isocyanate-reactive groups being 0.5:1 to 2.0:1.

A further subject of the present invention relates to a method for producing transparent polyurethanes by reaction of a composition comprising or consisting of A) a polyisocyanate component comprising 1,3- and/or 1,4-xylylene diisocyanate (XDI) produced or producible via gas-phase phosgenation in accordance with the present invention, and also, if desired, at least one further polyisocyanate having an isocyanate-group functionality of at least 2 per molecule, B) a polyol component comprising or consisting of at least one polyol having a hydroxyl-group functionality of at least 2 per molecule, and also, optionally, C) further auxiliaries and additives, the ratio of isocyanate groups to isocyanate-reactive groups being 0.5:1 to 15.0:1. Irrespective of the nature of the starting materials selected, in the method of the invention, the reaction of the polyisocyanate mixtures A) with the thiol component and/or with the polyol component and also, optionally with further components that are reactive toward isocyanate groups takes place with compliance with an equivalents ratio of isocyanate groups to isocyanate-reactive groups of 0.5:1 to 15.0:1, preferably of 0.7:1 to 2.0:1, more preferably of 0.8:1 to 1.2:1.

With the method of the invention, the components of the composition of the invention are mixed preferably, optionally in solvent-free form, in the above-indicated equivalents ratio of isocyanate groups to isocyanate-reactive groups, with the aid of suitable mixing assemblies, and are introduced by any desired techniques into open or closed molds, by means for example of simple casting by hand, but preferably with the aid of suitable machinery, such as the low-pressure or high-pressure machinery conventional in polyurethane technology or by the RIM process. Curing may be carried out in a temperature range from 40 to 180° C., preferably from 50 to 140° C., more preferably from 60 to 120° C., and optionally under an elevated pressure of up to 300 bar, preferably up to 100 bar, more preferably up to 40 bar.

The polyisocyanates and optionally the other starting components as well are here optionally degassed by application of vacuum.

In general, the moldings thus produced in accordance with the invention from the can be demolded after a short time, as for example after 2 to 60 min. This may optionally be followed by postcuring at a temperature of 50 to 100° C., preferably at 60 to 90° C.

In this way, compact polythiourethane bodies are obtained that are lightfast and weather-resistant, that possess high resistance toward solvents and chemicals, and also outstanding mechanical properties, in particular an excellent heat distortion resistance, even at relatively high temperatures of, for example, 80° C. Relative to the systems known to date, produced using diisocyanates generated by liquid-phase phosgenation, the moldings of the invention are distinguished by greater transparency and reduced hazing.

A further subject of the present invention relates to a compact transparent polythiourethane body or polyurethane body, obtainable by reacting the components of the composition of the invention. As already observed above, a compact transparent polythiourethane body generated in this way is particularly preferred on account of its good optical properties. The polythiourethane body or polyurethane body here may be a glass-substitute component, an optical, optoelectronic or electronic component, an optical lens, or a spectacle lens. Examples of specific applications are the production of or use as glass-substitute glazing, such as, for example, sun roofs, windscreens, rear windows or side windows in automotive or aircraft construction, as safety glass, solar modules, light-emitting diodes, lenses or collimators, of the kind employed, for example, as supplementary optical elements in LED lamps or automobile headlamps.

A particularly preferred field of use for the polythiourethane moldings of the invention obtainable from the compositions of the invention is, however, the production of lightweight polymeric spectacle lenses having high refractive index and high Abbe coefficient. Spectacle lenses produced in accordance with the invention are notable for outstanding mechanical properties, especially hardness and impact strength, and also good scratch resistance, and, furthermore, are easy to work and can be colored as desired.

The invention is discussed in more detail below, with reference to working examples and a FIGURE (FIG. 1).

EXPERIMENTAL SECTION AND EXAMPLES

Thermal Stability of Pure 1,3-XDA

By means of heating trials, the thermal decomposition of 1,3-XDA was investigated within the relevant boiling range of 220-240° C. For this purpose, 1,3-XDA was heated under a nitrogen atmosphere at the respective temperature for 8 hours, with samples being taken at the start and hourly thereafter to determine the nonvolatile fraction by GC analysis with internal standard.

GC Method for Determining 1,3-XDA with Internal Standard

Preparation of the standard solution: 1.4 g of anthracene were dissolved in 1 l of ethyl acetate in a volumetric flask at 23° C.

Sample preparation: about 1-2 g of the sample were admixed with exactly 20 ml of standard solution and homogenized Gas chromatograph: Hewlett Packard, HP 5890, series B Separating column: ZB 65 HT (from Zebron), fused silica, length 30 m, internal diameter 0.32 mm, film thickness 0.25 µm Temperatures: injector 250° C., detector (FID) 350° C., oven: start 80° C., hold time 0 min, heating rate 10° K/min to 350° C., hold time 10 min Carrier gas: helium, column pressure 1.0-1.1 bar abs., split vent 100 ml/h, septum purging 5-1 ml/h The results are compiled in Table 1.

Key:
Low boilers: area percent (area %) of low-boiling component with retention time 5.5 min.
1,3-XDA: area % of 1,3-XDA with retention time 9.5 min.
Nonvolatile (polyamines): 100%−(area % low boilers+area % 1,3-XDA)

TABLE 1 a
220° C.

| Component | Low Boilers | 1.3-XDA | Nonvolatile |
|---|---|---|---|
| 0 h | 0.01% | 99.29% | 0./70% |
| 1 h | 0.15% | 97.52% | 2.33% |
| 2 h | 0.31% | 95.90% | 3.79% |
| 3 h | 0.72% | 90.43% | 8.55% |
| 4 h | 2.01% | 88.22% | 9.77% |
| 5 h | 3.59% | 83.40% | 13.01% |
| 6 h | 5.05% | 74.64% | 20.31% |
| 7 h | 7.56% | 66.93% | 25.51% |
| 8 h | 11.45% | 54.91% | 33.64% | b
230° C.

| Component | Low Boilers | 1,3-XDA | Nonvolatile |
|---|---|---|---|
| 0 h | 0.08% | 98.01% | 1.91% |
| 1 h | 0.32% | 94.39% | 5.29% |
| 2 h | 0.70% | 90.92% | 8.38% |
| 3 h | 1.20% | 88.41% | 10.30% |
| 4 h | 3.12% | 83.85% | 13.03% |
| 5 h | 5.03% | 78.01% | 10.91% |
| 6 h | 7.92% | 68.51% | 23.57% |
| 7 h | 11.09% | 53.14% | 35.77% |
| 8 h | 15.49% | 33.64% | 50.87% | c
240° C.

| Component | Low Boilers | 1,3-XDA | Nonvolatile |
|---|---|---|---|
| 0 h | 0.11% | 98.74% | 1.15% |
| 1 h | 0.29% | 96.18% | 3.53% |
| 2 h | 2.06% | 91.61% | 6.33% |
| 3 h | 5.40% | 79.95% | 14.64% |
| 4 h | 10.60% | 70.21% | 19.20% |
| 5 h | 14.45% | 50.13% | 35.42% |
| 6 h | 19.78% | 33.42% | 46.81% |
| 7 h | 22.04% | 16.59% | 61.37% |
| 8 h | 7.48% | 0.00% | 92.52% |

The results of the heating trials showed that within the boiling range of technical relevance for gas-phase phosgenation, of 220-240° C., 1,3-XDA undergoes decidedly rapid decomposition to form nonvolatile polyamines.

Thermal Stability of Stabilized 1,3-XDA

The thermal decomposition of 1,3-XDA was investigated after addition of various stabilizers, by means of heating trials. For this purpose, 1,3-XDA, following addition of 500 ppm of the stabilizer in question was heated under a nitrogen atmosphere at 230° C. for 8 hours, with samples being taken at the start and hourly thereafter for GC analysis with internal standard. The fraction of nonvolatile polyamines was determined as indicated above and is compiled in Table 2.

Stabilizers: LONOL: 2,6-di-tert-butyl-p-cresol
DBSA: dodecylbenzenesulfonic acid
TINUVIN 571: alkylphenol-substituted benzotriazole (BASF)
p-TSA: p-toluenesulfonamide

TABLE 2

| Stabilizer | None | LONOL | DBSA | TINUVIN 571 | p-TSA |
|---|---|---|---|---|---|
| 0 h | 0.61% | 0.48% | 0.51% | 0.31% | 0.43% |
| 1 h | 5.29% | 0.50% | 0.59% | 0.41% | 1.07% |
| 2 h | 6.38% | 1.23% | 1.30% | 0.65% | 1.13% |
| 3 h | 10.30% | 1.58% | 1.62% | 0.73% | 1.38% |
| 4 h | 13.03% | 2.01% | 2.22% | 0.83% | 1.92% |
| 5 h | 16.91% | 2.53% | 2.73% | 0.98% | 3.65% |
| 6 h | 23.57% | 3.51% | 3.71% | 1.13% | 3.37% |
| 7 h | 35.77% | 4.23% | 4.34% | 1.28% | 4.80% |
| 8 h | 50.87% | 5.27% | 5.45% | 1.43% | 3.43% |

The results show that the thermal stability of 1,3-XDA within the boiling range technically relevant for gas-phase phosgenation, at 230° C., can be improved significantly by addition of stabilizers.

Implementation of the Phosgenation of 1,3-XDA

Example 1 (Inventive)

In a plant for gas-phase phosgenation with an amine evaporation stage in accordance with FIG. 1, a tubular reactor (L: 9350 mm, internal diameter 134.5 mm) having a coaxial nozzle (internal diameter 134.5 mm) arranged on the reactor axis, and a downstream isocyanate condensation stage, 200 kg/h of 1,3-XDA were vaporized continuously under a pressure of 650 mbar abs. with introduction of a nitrogen stream of 10 kg/h, the temperature in the pumping circuit (3200 kg/h) being held at 150° C. by cooling in a heat exchanger (WT). The pumping circuit was admixed beforehand with 500 ppm of TINUVIN 571. The admission temperature to the vaporizer (V) is 255° C., the entry temperature of the cooling medium into the heat exchanger (WT) is 40° C., and the mean residence time of the 1,3-XDA in the pumping circuit was 35 minutes. After leaving the vaporizer, the stream of gaseous 1,3-XDA and nitrogen was heated to 280° C. in a further heat exchanger, and supplied via the coaxial nozzle to the reactor. At the same time, in parallel, 750 kg/h of phosgene were heated to 310° C. and likewise supplied continuously to the reactor, at the annular space left free by the nozzle, the two reactant streams being mixed and reacted in the reactor. The rate of the gas flow in the reactor here was about 20 m/s, and the rate ratio of amine/nitrogen flow to phosgene flow was 8.8. The pressure at the vacuum pump was 600 mbar abs. After a mean residence time in the reactor of 0.48 s, the gas stream comprising the 1,3-XDI reaction product was cooled by injection cooling with monochlorobenzene and condensed, the temperature of the liquid phase in the quench being about 90° C. The amount of 3-chloromethyl benzylisocyanate, determined by gas chromatography, was 0.4%, based on the sum of 1,3-XDI and 3-Cl-XI. The reaction mixture was subsequently freed from HCl and phosgene, and worked up by distillation. The yield of 1,3-XDI amounts to 95% of theory.

Example 2 (Inventive)

In the plant described above, analogously, 160 kg/h of 1,3-XDA were vaporized under a pressure of 500 mbar abs. with introduction of a nitrogen stream of 4 kg/h, the temperature in the pumping circuit (3200 kg/h) being held at 150° C. by cooling in a heat exchanger (WT). The pumping circuit was admixed beforehand with 500 ppm of TINUVIN 571. The admission temperature to the vaporizer (V) is 240° C., the entry temperature of the cooling medium into the heat exchanger (WT) was 40° C., and the mean residence time of the 1,3-XDA in the pumping circuit was 43 minutes. The stream of gaseous 1,3-XDA and nitrogen was heated to 280° C. in a further heat exchanger, and supplied via the coaxial nozzle to the reactor. At the same time, in parallel, 500 kg/h of phosgene were heated to 310° C. and likewise supplied continuously to the reactor, at the annular space left free by the nozzle, the two reactant streams being mixed and reacted in the reactor. The rate of the gas flow in the reactor here was about 20 m/s, and the rate ratio of amine flow to phosgene flow was 8.8. After a mean residence time in the reactor of 0.46 s, the gas stream comprising the 1,3-XDI reaction product was cooled by injection cooling with monochlorobenzene and condensed, the temperature of the liquid phase in the quench being about 90° C. The amount of 3-chloromethyl benzylisocyanate, determined by gas chromatography, was 0.3%, based on the sum of 1,3-XDI and 1,3-Cl-XI. The reaction mixture is subsequently freed from HCl and phosgene, and worked up by distillation. The yield of 1,3-XDI amounts to 92% of theory.

Production of XDI produced via liquid-phase phosgenation, for comparison:

Example 3 (Comparative)

With stirring and cooling, a solution of 5 parts by weight of 1,3-XDA in 50 parts by weight of monochlorobenzene is metered at 0-10° C. to a solution of 20 parts by weight of phosgene in 25 parts by weight of monochlorobenzene, and, after the end of addition, the solution is allowed to come to room temperature. The temperature is subsequently raised to reflux, with phosgene being introduced in line with the evolution of gas, and phosgenation is continued until the solution gradually becomes clear. As soon as the clearpoint has been reached (about 4-5 h), phosgenation is continued for 30 minutes. The introduction of phosgene is then ended and, with introduction of nitrogen, the reaction mixture is boiled at reflux until phosgene is no longer detectable in the offgas.

The amount of 3-chloromethylbenzyl isocyanate, determined by gas chromatography, is 0.9%, based on the sum of 1,3-XDI and 1,3-Cl-XI. The reaction mixture is subsequently worked up by distillation, giving XDI as a colorless liquid having a boiling point of 130° C./0.2 mbar. The yield of 1,3-XDI amounts to about 80% of theory.

Example 4 (Inventive)

2 kg of the XDI obtained in Example 2 were subjected to fractional distillation on a column. The first 500 g were discarded as an initial fraction; obtained as a main fraction are 1 kg of colorless 1,3-XDI. This main fraction was admixed at room temperature with 1.4 g of ZELEC UN (Steppan) and left to stand for 24 hours. The HC content of the sample, measured according to ASTM specification D4663-98 after distillation, was 105 ppm.

Example 5 (Comparative)

2 kg of the XDI obtained in a similar manner as in Example 3 were subjected to fractional distillation on a column. The first 800 g were discarded as an initial fraction; obtained as a main fraction are 700 g of colorless 1,3-XDI. This main fraction was admixed at room temperature with 0.98 g of ZELEC UN and left to stand for 24 hours. The HC content of the sample, measured according to ASTM specification D4663-98 after distillation, was 108 ppm.

Production of polythiourethane spectacle lenses:

Example 6 (Inventive)

First of all a casting mold was produced, by clamping together two glass mold shells (85 mm diameter, internal radius 88 mm, Shamir Insight, Inc., IL) at a distance of 8 mm with a polymeric sealing ring, to form a casting cavity. The mold distance at each location on the lens was 8 mm.

The casting system was produced as follows:

In a flask, 94.59 g of 1,3-XDI from Example 4 were dissolved in 0.002 g of dibutyltin dichloride (DBC) and evacuated at 10 mbar for 30 minutes. 90.00 g of DMPT (4-mercaptomethyl-1,8-dimercapto-3,6-dithiaoctane, Bruno Bock GmbH, used as obtained) were subsequently added to the flask, and the final mixture was stirred and degassed for 30 minutes at 10 mbar. This mixture was then filtered through a 5 μm filter, drawn up onto a syringe, and used to fill the casting mold fully.

The filled casting mold was cured in a drying oven with the following temperature profile: heating for 15 hours at 65° C.; 2 hours at 100° C.; and a further 2 hours at 120° C. Thereafter the casting mold was cooled to room temperature and, following complete cooling, first the sleeve and then the two glass elements were removed manually.

In this way, a clear, transparent and haze-free spectacle lens blank was obtained. The refractive indices and Abbe coefficients were measured on an AR4D model Abbe refractometer from A. KRÜSS Optronic GmbH at 23° C.

Under the D65 standard illuminant, the transmittance was 90.3% and the haze was 2.1. The refractive index nE was 1.67 at 23° C. The transmittance and haze measurements were carried out in accordance with ASTM D 1003 using a Haze-Gard Plus from Byk under standard illuminant D65 (defined in DIN 6173).

Example 7 (Comparative)

In the same way as for Example 6, a spectacle lens blank was produced using 1,3-XDI from Example 5. This spectacle lens blank was completely hazy; the transmittance was 29.7%, the haze 100, and measurement of the refractive index was not possible.

The invention claimed is:
1. A method for producing 1,3- and/or 1,4-xylylene diisocyanate (XDI) by phosgenation of 1,3- and/or 1,4-xylylenediamine (XDA) with phosgene in the gas phase in a reactor connected to a vaporizer circuit, the method comprising:
vaporizing xylylenediamine/xylylenediamines in a vaporizer in the vaporizer circuit, optionally with addition of stabilizers and/or an inert gas, at a pressure of <1000 mbar, with a mean residence time in the vaporizer circuit of 5 to 90 minutes and at a temperature in a pumping circuit connected to the vaporizer circuit of 40 to 190° C., wherein the temperature is maintained by cooling in a first heat exchanger in the pumping circuit,
heating XDA vapors a further 10-100° K. above the vaporization temperature of the XDA at prevailing pressure in a second heat exchanger in the pumping circuit, and
reacting the vapors from the second heat exchanger connected to the reactor with phosgene by gas-phase phosgenation in the reactor.
2. The method according to claim 1, wherein the xylylenediamine/ xylylenediamines is vaporized at 350 to 900 mbar.

3. The method according to claim 1, wherein the xylylenediamine/ xylylenediamines is vaporized at 500 to 800 mbar.

4. The method according to claim 1, wherein the mean residence time in the vaporizer circuit is 10 to 60 minutes.

5. The method according to claim 1, wherein the mean residence time in the vaporizer circuit is 10 to 45 minutes.

6. The method according to claim 1, wherein the temperature in the pumping circuit of the vaporization is 60 to 170° C.

7. The method according to claim 1, wherein the temperature in the pumping circuit of the vaporization is 60 to 150° C.

8. The method according to claim 1, wherein the XDA vapors are heated by a further 20 to 50 K above the vaporization temperature of the XDA under prevailing pressure, and then reacted with phosgene via gas-phase phosgenation.

9. The method according to claim 1, wherein the XDA is admixed prior to vaporization with one or more stabilizers in concentrations of 50-2000 ppm based on XDA.

10. The method according to claim 9, wherein the stabilizers are sterically hindered phenols and/or alkyl-substituted benzosulfonic acids.

11. The method according to claim 1, wherein XDA droplets are separated by a droplet separator between the steps of vaporization of the XDA in the vaporizer circuit and superheating of the XDA vapors in the pumping circuit and/or after superheating of the XDA vapors in the pumping circuit.

12. The method according to claim 11, wherein the apparatus used for the superheating also functions as droplet separator(s).

* * * * *